(12) United States Patent
Cabilly et al.

(10) Patent No.: US 6,562,213 B1
(45) Date of Patent: May 13, 2003

(54) ELECTROPHORESIS APPARATUS FOR SIMULTANEOUS LOADING OF MULTIPLE SAMPLES

(75) Inventors: Shmuel Cabilly, Gedera (IL); Uri Yogev, Herzelia (IL); Ilana Margalit, Ramat Gan (IL)

(73) Assignee: Ethrog Biotechnology Ltd., Ness Ziona (IL)

( * ) Notice: Subject to any disclaimer, the term of this patent is extended or adjusted under 35 U.S.C. 154(b) by 96 days.

(21) Appl. No.: 09/651,087

(22) Filed: Aug. 30, 2000

(51) Int. Cl.[7] .................. G01N 27/447; G01N 27/453; C12M 3/00; C12M 1/34
(52) U.S. Cl. ............... 204/456; 204/466; 204/605; 204/616; 435/288.4; 435/305.2
(58) Field of Search ................. 204/456, 466, 204/605, 616; 435/288.3, 288.4, 305.1, 305.2

(56) References Cited

U.S. PATENT DOCUMENTS

| | | | |
|---|---|---|---|
| 4,018,662 A | | 4/1977 | Ruhenstroth-Bauer et al. |
| 4,130,471 A | | 12/1978 | Gunbaumr |
| 4,305,799 A | * | 12/1981 | Schwarz et al. ............ 204/455 |
| 5,656,145 A | | 8/1997 | Nguyen et al. |
| 5,785,835 A | | 7/1998 | Saito et al. |
| 5,843,295 A | | 12/1998 | Steiner et al. |
| 5,972,188 A | | 10/1999 | Rice et al. |
| 6,013,166 A | | 1/2000 | Heller |
| 6,068,752 A | | 5/2000 | Dubrow et al. |
| 6,071,396 A | | 6/2000 | Day |

FOREIGN PATENT DOCUMENTS

| | | | |
|---|---|---|---|
| JP | 362066153 A | * | 3/1987 |
| WO | WO 00/16084 | | 3/2000 |

OTHER PUBLICATIONS

JAPIO abstract of Sugihara et al. (JP 362066153 A).*
Computer translation of Kazunobu et al. (JP 2000-060554).*

* cited by examiner

Primary Examiner—T. Tung
Assistant Examiner—Alex Noguerola
(74) Attorney, Agent, or Firm—Eitan, Pearl, Latzer & Cohen Zedek, LLP.

(57) ABSTRACT

Apparatus for simultaneous loading of multiple samples for molecular separation, including a separation area with walls, at least one of the walls has apertures having loading sites, a gel located within the separation area, and a plurality of wells within the gel. The loading sites are offset with respect to the wells. The apertures are connected to the plurality of wells by channels structurally configured to convey samples from the apertures to the wells, and apparatus for electrophoresis separation having an electrophoresis area, an electrophoresis gel located within the electrophoresis area, and multiple rows of wells within the electrophoresis gel, wherein the rows are arranged in an alternating staggered format. A method for simultaneous loading of multiple samples into the electrophoresis apparatus.

63 Claims, 4 Drawing Sheets

ELECTROPHORESIS APPARATUS FOR SIMULTANEOUS LOADING OF MULTIPLE SAMPLES

FIELD OF THE INVENTION

The present invention provides an apparatus for simultaneously loading multiple samples for conducting an electrophoresis test.

BACKGROUND OF THE INVENTION

A great deal of diagnostic procedures and laboratory research are carried out wherein DNA, RNA or proteins are separated according to their physical and chemical properties via electrophoresis. This process is widely used and has many applications. For example, electrophoresis is used to analyze DNA molecules according to their resultant size after being digested by restriction enzymes. It is also used to analyze the products of a polymerase chain reaction (PCR).

In some instances, molecules are driven toward a capture layer, which has part of a molecular recognition pair e.g. antibody-antigen, DNA-DNA probe, biotin-avidin, ligand-receptor, lectin-carbohydrate or others. Only specific parts of each pair of molecules that move through the capture layer are captured (e.g., an antigen when the capture layer contains a specific antibody), while the non-specific molecules pass through the layer unimpeded.

Electrophoresis separation is carried out in a separation medium, such as a gel of agarose or acrylamide or a combination of the two. Agarose gels are cast in open trays and form a horizontal slab whereas acrylamide gels are vertically cast between two glass plates.

Prior to electrophoresis separation, wells are introduced into the gel for sample deposition by applying a comb-like structure prior to the solidification or polymerization of the gel matrix. A row of approximately 8-15 wells is formed across one end of the gel.

In order to effect the electrophoresis separation, two opposite ends of the gel are exposed to a buffered solution which is connected by electrodes, often made of platinum, to an electrical power source. Once the electrical power source is switched on, the electric field forces negatively charged molecules to move towards the anode and positively charged molecules to move towards the cathode. DNA is negatively charged and therefore, in the agarose or acrylamide gels which provide sieving action, DNA molecules move towards the anode at a rate which depends on their size, wherein the smaller the molecules the faster they move. The running distance should be long enough to allow sufficient differentiation between molecules.

It is desirable to visualize and to document the results of the electrophoresis separation test. In electrophoresis separation of DNA molecules, this has been done by immersing the gel slab after the electrophoresis separation has been completed in a solution of a fluorescent compound, such as ethidium bromide, which intercalates within DNA molecules and emits visible light when exposed to an ultraviolet (UV) light. In order to document the results, a picture of the gel is taken through one of various photographic means.

Prior art electrophoresis systems are potential sources of contamination to the working environment in which the tests are performed. The two major sources of contamination are ethidium bromide and PCR products. Ethidium bromide is a hazardous chemical due to its mutagenic activity and therefore, exposure to ethidium bromide may induce malignant tumors. PCR is an extremely sensitive method to the extent that a single molecule of DNA product from one PCR (out of the trillions of molecules being produced) may interfere with the subsequent PCR such that it will produce incorrect results.

Also, conventional electrophoresis is time consuming in terms of preparation and handling. This is particularly true when a large number of samples are to be analyzed, and loading of samples is done one by one.

Several inventions have been directed towards eliminating contamination, such as U.S. Pat. No. 5,972,188, which describes the use of a membrane loader for gel electrophoresis; and an electrophoresis apparatus with a cover, in U.S. Pat. Nos. 5,582,702, and 5,865,974 incorporated herein by reference. The apparatus is directed towards the running of electrophoresis separation, as well as detecting and analyzing the results, within a self-contained, disposable unit.

Attempts have been made to reduce the time it takes to run an electrophoresis separation as well by loading many samples at once. Further, simultaneous loading of samples could reduce contamination and human error. Standards in cell culture, ELISA and PCR analysis provide different sized plates, with corresponding pipettes for ease in sample loading and analysis. For example, 96-well plates are typically used. Correspondingly, pipettes that fit this configuration are available and are widely used. Use of standard microtiter pipettes would greatly reduce the loading time for electrophoresis.

Saito et al., in U.S. Pat. No. 5,785,835, address this issue by providing an apparatus for loading of samples into wells within an exposed gel with standard pipettes. However, the testing apparatus has limited resolution capacity since a running distance of only 0.8 cm is available. In U.S. Pat. No. 6,071,396 a gel-matrix layer is described with wells arranged for loading of samples with standard pipettes. In this patent, the running distance is increased by diagonally offsetting the entire array of wells. U.S. Pat. No. 6,013,166 describes a method for reducing the linear dimension necessary for electrophoresis separation in a microgel format.

In addition, several needle guide designs have been developed to aid in loading samples directly into wells in a way that would save time and prevent inaccuracies. For example, U.S. Pat. No. 5,656,145 provides a needle guide for loading samples into a vertical slab gel. Similarly, U.S. Pat. No. 5,843,295 is directed towards a combination comb/loading guide unit. In both of these designs, the loading sites are positioned directly on top of the wells so as to allow for simple, direct loading of samples.

SUMMARY OF THE INVENTION

This invention provides, in accordance with an embodiment of the present invention, an apparatus for simultaneous loading of multiple samples for molecular separation, including a separation area with walls wherein at least one of the walls has multiple apertures with loading sites, a gel located within the separation area, and a plurality of wells within the gel. The apertures are connected to the plurality of wells by channels structurally configured to convey samples from the apertures to the wells. In one embodiment, the loading sites are spaced at predetermined intervals so as to conform with intervals between tips on a loader.

In one embodiment, the plurality of wells is arranged in rows, and the rows are arranged in stagger format, providing a running distance for molecular separation which is longer than the distance between two adjacent rows.

There is provided, in accordance with another embodiment of the present invention an apparatus for electrophoresis separation having a substantially closed electrophoresis area, an electrophoresis gel located within the electrophoresis area, and multiple rows of wells within the electrophoresis gel, wherein the rows are arranged in a stagger format.

There is provided, in accordance with another embodiment of the present invention, a gel layer for molecular separation having a plurality of wells within the gel layer. The wells are arranged in a plurality of rows, and wells of one row are horizontally shifted from wells of a neighboring row by a predetermined distance. The horizontal shift is alternated from left to right, so as to form a staggered format of wells within the gel layer.

There is provided, in accordance with another embodiment of the present invention a device for delivering samples into wells for molecular separation, having a flat surface with a top side and a bottom side, multiple loading sites on the top side arranged in standard format, multiple apertures on the bottom side arranged in stagger format and leading to the wells, and a channel through the flat surface connecting the loading sites to the apertures.

There is provided, in accordance with another embodiment of the present invention an electrophoresis apparatus for non-weighted sample deposition, including a substantially closed area, an electrophoresis gel with wells located within the electrophoresis area, and a non-liquid ion source located within the gel, eliminating the need for weighting samples before deposition into the wells.

There is provided, in accordance with another embodiment of the present invention a system for conducting electrophoresis separation including an electrical power source, a substantially closed disposable cassette for conducting an electrophoresis separation therein and having conductive elements therein, and a support for supporting the substantially closed cassette and for connecting the electrical power source to the conductive elements of the cassette, where one or more gels may be connected simultaneously. The cassette includes a body of gel for carrying therein the electrophoresis separation, a plurality of wells in the body of gel arranged in a stagger format and a plurality of apertures having loading sites leading to the plurality of wells.

There is provided, in accordance with another embodiment of the present invention a method for treating water-absorbent plastic used for electrophoresis devices, including the steps of placing the water-absorbent plastic in a humidified environment and saturating the water-absorbent plastic by leaving it in a humidified environment for a predetermined period of time.

There is provided, in accordance with another embodiment of the present invention a method for simultaneous loading of multiple samples into an electrophoresis apparatus, including the steps of providing an electrophoresis apparatus having an area with walls defining the area and a gel within the area having multiple wells arranged in stagger format, wherein the walls include apertures having loading sites and channels structurally configured to direct samples into the wells, loading the samples into the openings with a standard multiple loading mechanism, and directing the samples from the apertures to the wells.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
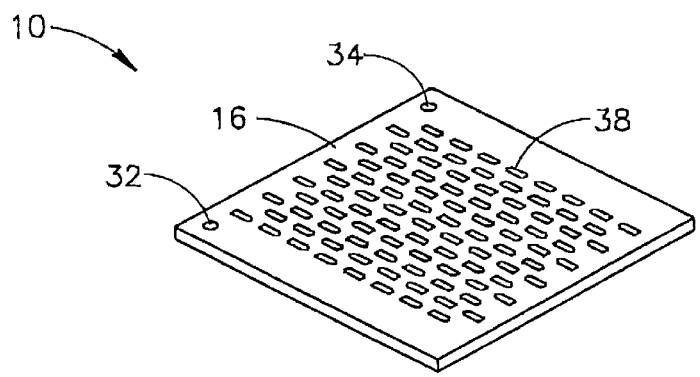
FIGS. 1 and 2 are schematic illustrations of an electrophoresis apparatus in accordance with an embodiment of the present invention.
Figure 1:
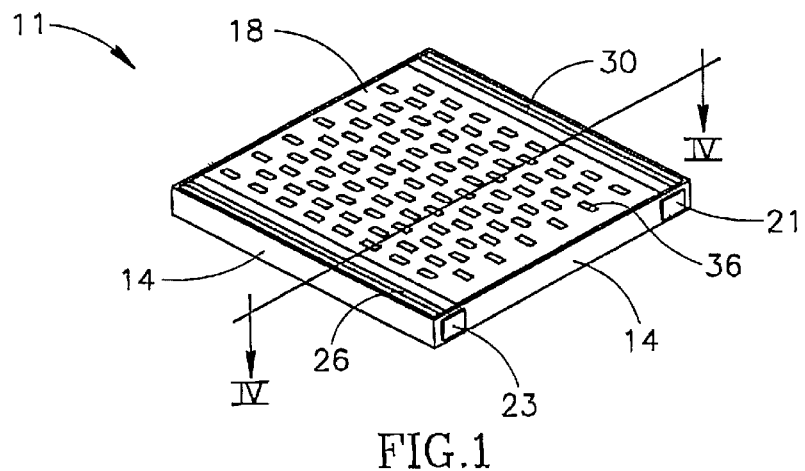
Figure 2:
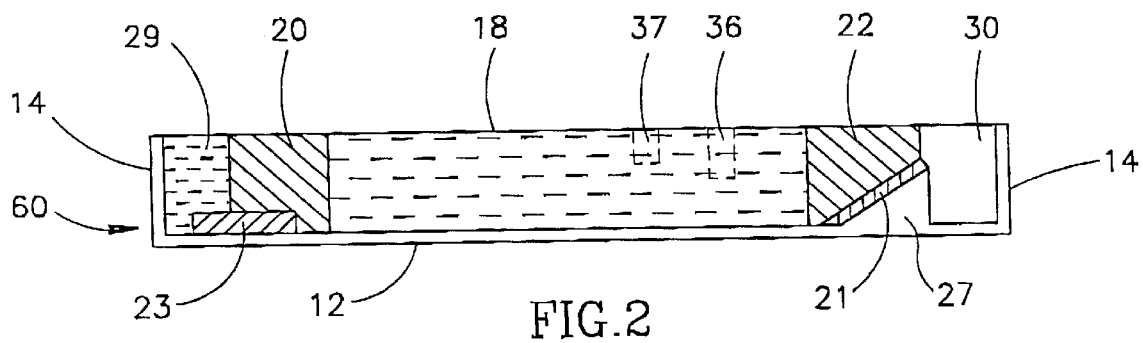

Reference is made to FIGS. 1 and 2, which illustrate an electrophoresis disposable cassette, generally referenced 10. FIG. 1 shows an external configuration of cassette 10, while FIG. 2 shows a cross-sectional view. Cassette 10 is a closed disposable cassette used for a single electrophoresis test, and includes all the chemical compounds required for driving the electrophoresis separation and for enabling visualization of its results when DNA as well as RNA or protein molecules have been separated, as will be described hereinbelow.

As shown in FIG. 1, cassette 10 comprises a three dimensional separation area 11 having bottom wall and side walls, referenced 12 and 14 respectively, and a top wall 16 having a specified thickness. Cassette 10 is substantially closed in that it is enclosed by walls 12, 14 and 16, but it also comprises vent holes and apertures as will be described hereinbelow. In one embodiment, the thickness ranges from 0.1–10 mm, In another embodiment, the thickness is 1.5 mm. Cassette 10 as shown in FIG. 1 has a specified length, width and height. In one embodiment, the length ranges from 100–200 mm, the width ranges from 50–150 mm and the height ranges from 1–10 mm. In a preferred embodiment, length, width and height are 160 millimeters (mm), 100 mm and 6 mm, respectively, In another preferred embodiment, length, width and height are 130 mm, 130 mm and 6 mm, respectively.

Bottom wall 12 and top wall 16 are preferably made of any suitable UV transparent material, such as the TPX plastic commercially available from MITSUI of Japan or the Polymethylmethacrylate (PMMA) plastic commercially available from Repsol Polivar S.P.A. of Rome, Italy. Cassette 10 may include vent holes 32 and 34 to allow for gaseous molecules that might be generated due to the electrochemical reaction (e.g., oxygen and/or hydrogen) to be released. In one embodiment, vent holes range in diameter from 0.5–2 mm. In a preferred embodiment, vent holes are 1 mm in diameter.

As seen in the cross section illustration (IV—IV) of FIG. 2, area 11 comprises a get matrix 18 which may be any suitable gel matrix for electrophoresis, such as an agarose gel or a gel made of acrylamide (available from, for example, Sigma, St. Louis, Mo., USA). A plurality of wells 36 may be introduced into gel 18, by using a "comb" having a row of protruding teeth positioned so that the teeth project into the gel layer while it sets. In one embodiment, the plurality of wells ranges from 1–200 wells. In another embodiment, the plurality of wells ranges from 8–12 wells. In another embodiment, the plurality of wells included 96 wells, When the gel has set, the comb Is removed to leave a row of wells 36, or holes, in the layer. In one embodiments wells 36 are dimensions of 0.5–5 mm wide, 1–5 mm long, and 3–5 mm deep, and are used to introduce samples of the molecules to undergo molecular separation. One row or several rows may be formed. In one embodiment of the present invention, 12 rows of 8 wells per row are formed, and are arranged in a stagger format, as shown in FIG. 1 and described more fully below. In another embodiment, 8 rows of 12 wells per row are formed and may also be arranged a stagger format. For one embodiment of the present invention, top wall 16 has apertures used as loading sites 41, as described more fully below.

In addition, cassette 10 may optionally include a capture layer 37 including part of a molecular on pair for separating samples according to binding properties. Capture layer 37 is immobilized within gel 18, and is fabricated with resins to which the binding site of a molecule of interest will covalently bind. Some examples include avidin on acrylic beads, biotin on cross linked beaded agarose and others. The resins are mixed with agarose or other materials and poured as layers into gel 18. Alternatively, acrydite™ (available from Mosaic Technologies, Waltham, Mass., USA) may be used. Acrydite™ is a phosphoramide that is capable of copolymerization with acrylamide, and it can be used to introduce copolymerizable groups on the 5' terminus of any oligonucleotide probe. To make the capture layer, Acrydite™ oligonucleotide capture probes may be mixed with acrylamide solutions and polymerized into gel layers.

The capture electrophoresis technique provides concentrated signals, saves time and saves material. One or multiple capture layers may be used. This technique may be performed on its own, or in combination with a standard size electrophoresis separation.

It is desirable to visualize and to document the results of the electrophoresis separation test. In electrophoresis separation of DNA molecules, this has been done by immersing the gel slab after the electrophoresis separation has been completed in a solution of a fluorescent compound which emits visible light when exposed to an ultra violet (UV) light. According to one embodiment of the present invention, the samples or the gel interact with ethidium bromide or other fluorescent dyes. In this way, the results may be viewed in situ, without the need for exposing the samples to contamination by removing the gel from the enclosed area 11.

According to another embodiment of the present invention, various types of light sources may be used. In one embodiment, a light source of adjustable or non-adjustable wavelengths.may be used. The light source may include visible or non-visible light.

Alternatively a calorimetric dye, such as Methylene Blue may be added to the samples, the gel, or the ion reservoir and may interact with the molecules undergoing electrophoresis separation, so as to enable visualization of the results without the need for a UV light source.

Area 11 also comprises two conductive electrodes referenced 21 and 23 which, when connected to an external direct current (DC) electrical power source, provide the electric field required to drive electrophoresis separation. In the illustrated embodiment, electrode 21 is the cathode and electrode 23 is the anode. The system may also include a support for connecting conductive elements of cassette 10 to the power source. In one embodiment, the support is configured to connect to one or more gels simultaneously. Further, the system optionally includes a camera for documentation.

In one embodiment, the gel 18 and the conductive electrodes 21 and 23 are in contact with non-liquid Ion sources such as ion exchange matrices as described in U.S. Pat. Nos. 5,582,702 and 5,865,974.

It should be noted that since plastics used as cassette material are sometimes water absorbent, they may be pretreated by placement in a humidified environment and saturation by leaving it for a predetermined period of time so as to avoid later water adsorption or uptake of liquid, thereby keeping the gel intact, In one embodiment, the period of time ranges from 1–72 hours. In another embodiment, the period of time ranges from 1–20 days. In another embodiment, the period of time is at least 10 days. In a preferred embodiment, the period of time is 10 days.

It should be noted that in conventional electrophoresis, samples must be weighted so that they sink through the buffer to the bottom of the wells. This is generally accomplished by combining a substance such as Glycerol, Sucrose, or Ficoll polymer with the sample. It will be appreciated that in one embodiment of the present invention, there is no liquid buffer present in the vicinity of the wells, and instead, a non-liquid ion source is located within said gel. Thus, the step of weighting samples before deposition into said wells may be eliminated, thereby decreasing the time necessary to perform an experiment.

Figure 3A:
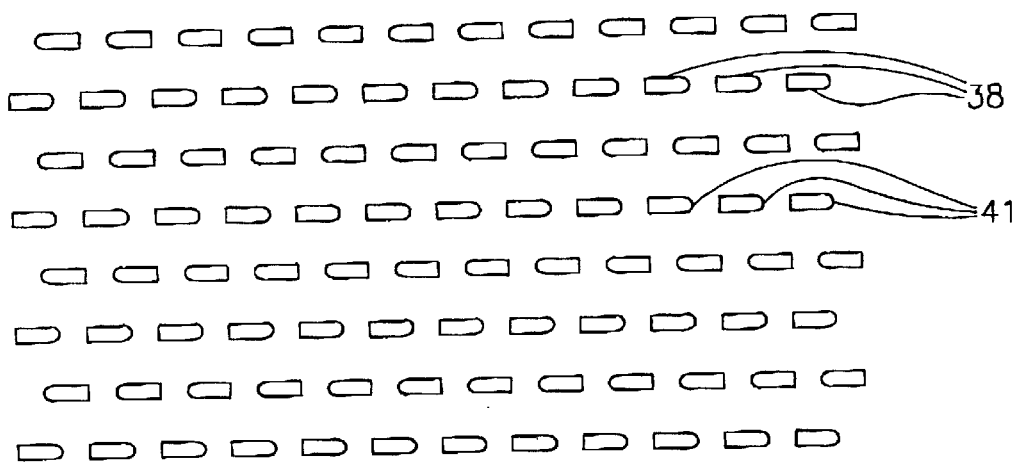
FIGS. 3A–3D are geometric illustrations of configurations of wells and apertures and loading sites according to one embodiment of the present invention.
Figure 3B:
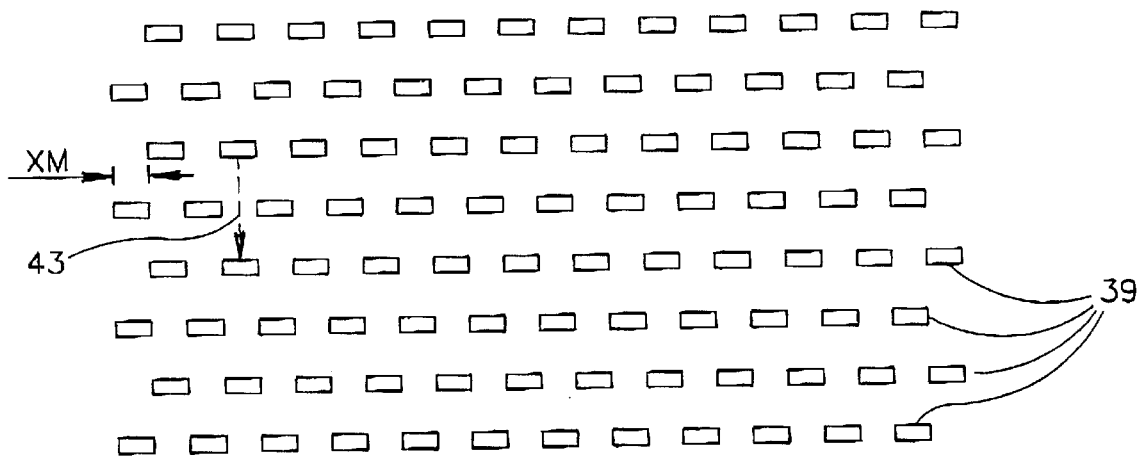
Figure 3C:
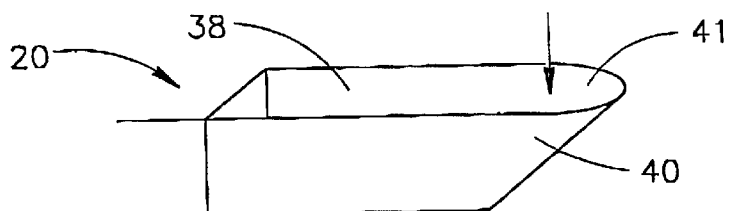
Figure 3D:
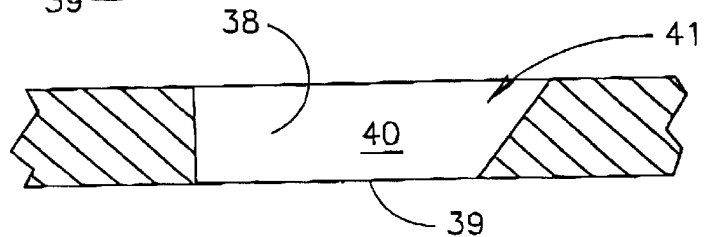
Figure 4A:
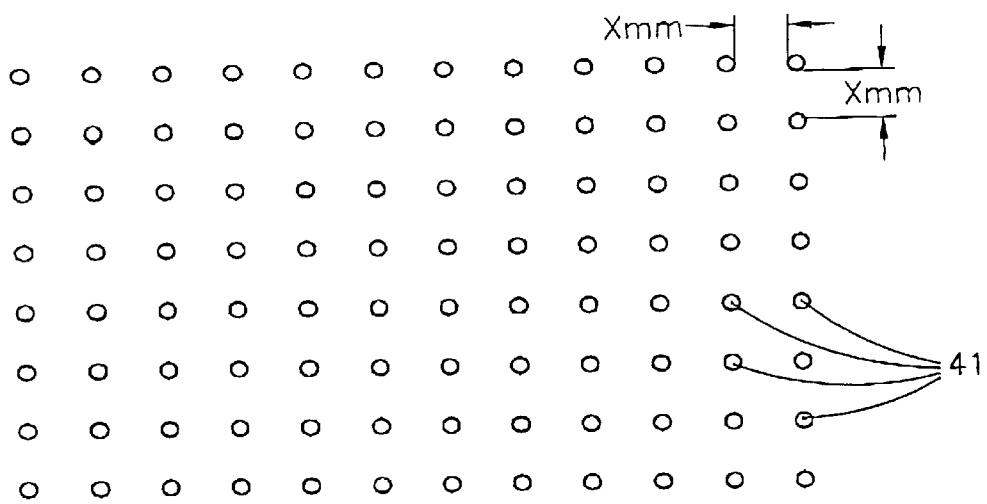
FIGS. 4A–4C are geometric illustrations of configurations of wells and apertures and loading sites according to another embodiment of the present invention.
Figure 4B:
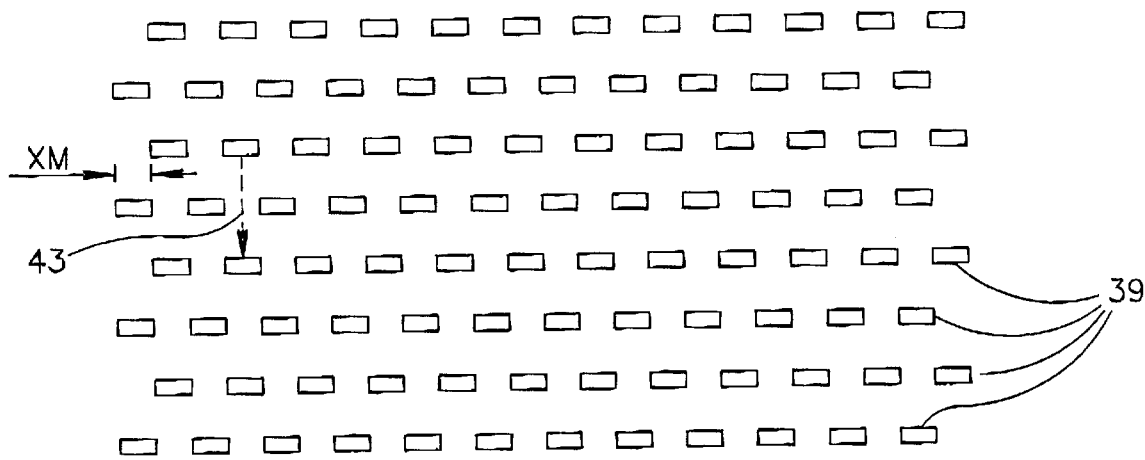

Reference is now made to FIGS. 3A–3D, taken together with 4A–4C, which show embodiments of loading sites 41 and outlet apertures 39 on two sides of wall 16. It will be appreciated that in one embodiment, wall 16 refers to the top wall, or the cover, of the apparatus. In another embodiment, other walls are used, such as side walls. Wall 16 should be considered as a flat surface with a top side and a bottom side. FIGS. 3A and 4A show views from the top side of wall 16. FIGS. 3B and 4B show views from the bottom side of wall 16. FIG. 3C shows a three-dimensional view of a portion of wall 16. FIGS. 3D and 4D show cross-sectional views of a portion of wall 16.

Stagger format of outlet apertures 39, located on the bottom side of wall 16, corresponds to stagger format of wells 36 within a layer of gel 18, as depicted in FIGS. 3B and 4B. That is, wells of one row are horizontally shifted from wells of a neighboring row by a predetermined distance. In one embodiment, the predetermined distance is in the range of 0.05–20 mm. In another embodiment, the predetermined distance is 4.5 mm. The horizontal shift occurs in alternating directions from left to right, so as to form a staggered format.

Thus, when electrophoresis separation takes place, the available running distance between adjacent wells 36 in the direction of electrophoresis separation is from 8–20 mm. In one embodiment, the available running distance is up to 18 mm, as shown by arrow 43. This amount is double what would be available without stagger formatting, greatly increasing the potential for larger sized molecules to be separated. If wells 36 were arranged according to a standard format, and not a stagger format, samples in each row would have a running distance of less than 1 cm, whereas in the configuration illustrated in FIG. 3B, twice that distance is available since samples can run between wells 36 of the next row.

In the embodiment shown in FIG. 3A, inlet apertures 38 have loading sites 41 located on the edges, all on the top of wall 16 of cassette 10. Loading sites 41 are configured either linearly (one row), or in a geometrical arrangement of columns and rows, typically in a rectangular arrangement In one embodiment, loading sites 41 are spaced at predetermined intervals so as to conform with intervals between tips on a loader. "Loader" refers to a mechanism used to load samples, such as a micro-titer pipette, as described hereinbelow. Multiple loading mechanisms allow for many samples to be loaded at once. Thus, the spacing between loading sites can vary, and may be configured to conform with intervals on any type of loader. In one embodiment, the predetermined intervals include 0.5–2 mm spacings. In a preferred embodiment, the predetermined intervals include 9 mm spacings, so as to conform with a micro-titer multi-pipette loader for 96 wells. In another embodiment, predetermined intervals include 0.001–1 mm spacings, so as to allow for a micro-scale system.

The shape of loading sites 41 may vary, but they are typically circular, so as to fit the end of a loader tip. A standard multiple loading mechanism such as a micro-titer multi-pipette loader available from, for example, Eppendorf Scientific, Inc., Westbury, N.Y., USA may be used, thus enabling simultaneous loading of as many samples as can fit in the pipette. Thus, for a 96-well configuration, loaders are available from, for example, Beckman Coulter, Inc., Fullerton, Calif., USA, that would enable loading of 96 samples all at the same time, or loading of 8 or 12 samples at a time. Similar models might be available for the other formats as well.

Loading sites 41, either located on the edges of inlet apertures 38 as in FIG. 3A, or alone, as in FIG. 4A, are not directly above outlet apertures 39, which lead into wells 36. Therefore, samples must be conveyed to wells 36, either by use of an incline, or by some other method, as described hereinbelow. Variations of the described embodiments are possible, for example, apertures and loading sites located in walls other than wall 16, such as side walls which in a vertical gel would form the top wall.

Figure 4C:
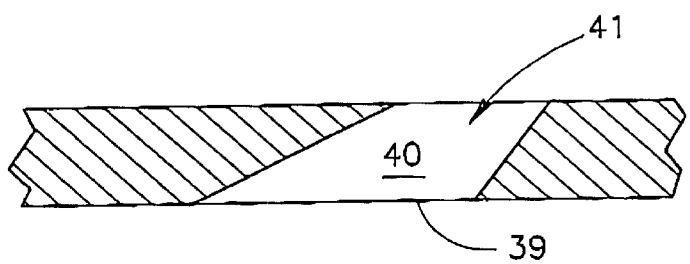

As shown in FIGS. 3D and 4C, channels 40 connect loading sites 41 to outlet apertures 39. Channels 40 are formed from structural adaptations of wall 20 connecting loading site 41 to outlet aperture 39 so as to allow for the flow of a sample from loading site 41 to outlet aperture 39. Channels 40 are structurally configured in such a way so as to convey samples into wells 36. In one embodiment, channel 40 comprises an incline. In another embodiment, channel 40 comprises another feature to help convey the sample, such as a magnetic or electrical property.

Figure 5:
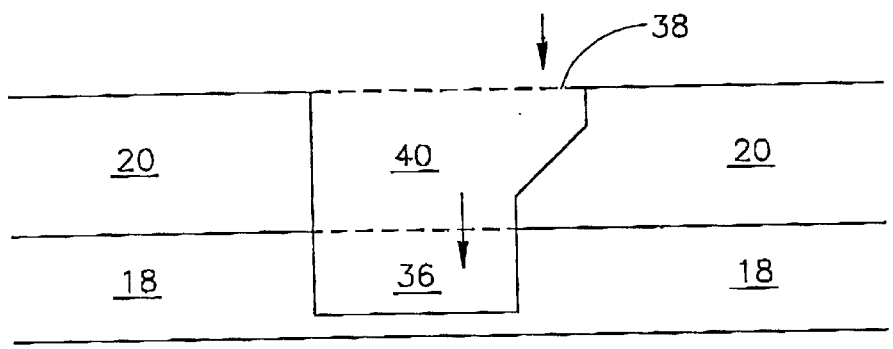
FIG. 5 is a schematic illustration of a channel configuration in accordance with one embodiment of the present invention.

Reference is now made to FIG. 5, which shows an embodiment of the present invention. A wide loading site 41 is portrayed above outlet aperture 39, Thus, the shape and/or size of loading site 41 differs from the shape and/or size of outlet aperture 39. In this example, channel 40 is configured in an irregular shape so as to allow for the sample to be directed into outlet aperture 39, even though application of the sample may not occur directly in line with outlet aperture 39.

Figure 6:
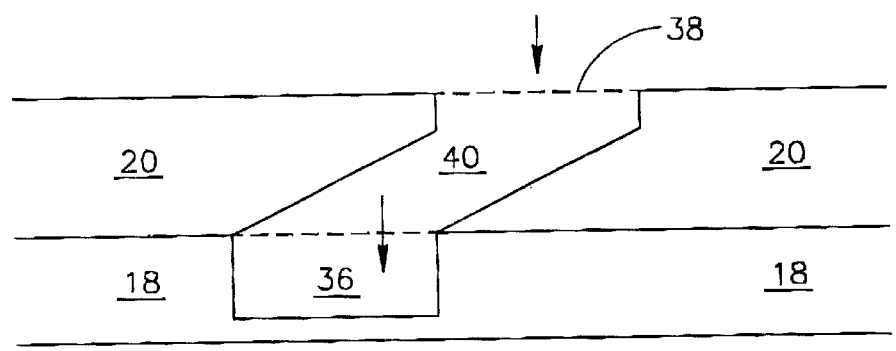
FIG. 6 is a schematic illustration of a channel configuration in accordance with another embodiment of the present invention.

Reference is now made to FIG. 6, which shows a further embodiment of the present invention. Outlet aperture 39 and loading site 41 are indirectly aligned with one another. Since loading site 41 is not located directly above outlet aperture 39, an incline in channel 40 provides direction of the sample into outlet aperture 39, and then into well 36.

Figure 7A:
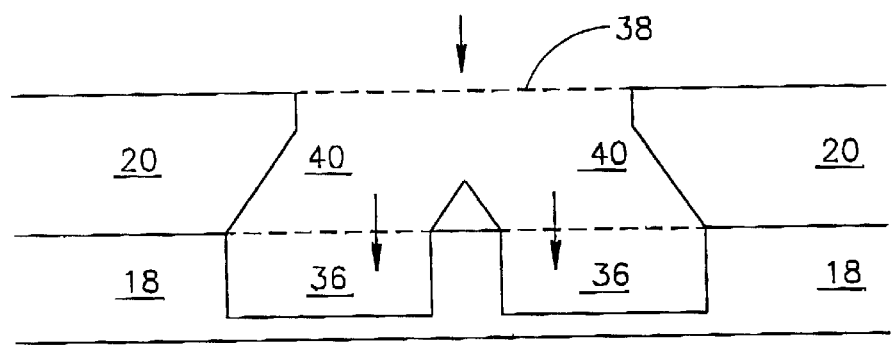
FIGS. 7A and 7B are schematic illustrations of channel configurations in accordance with further embodiments of the present invention.
Figure 7B:
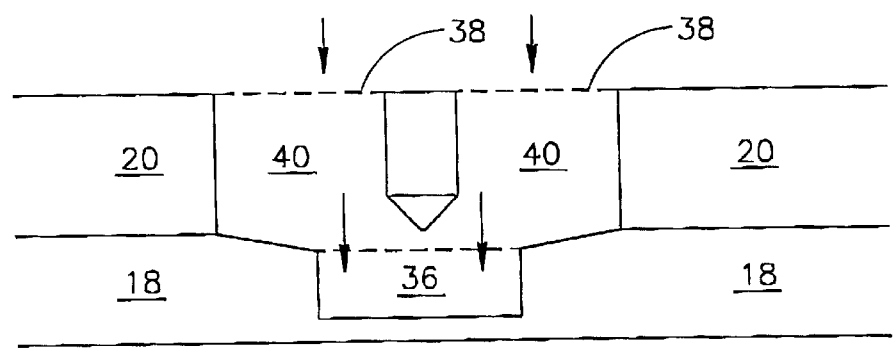

Reference is now made to FIGS. 7A and 7B, which are illustrations of further embodiments of the present invention. In FIG. 7A, one loading site 41 leads to multiple outlet apertures 39, and in FIG. 7B, multiple loading sites 41 lead to one outlet aperture 39. Thus, as shown in FIG. 7A, multiple tests can be performed on a sample after a single pipette application, reducing the sample loading time. This is accomplished by channel 40 having a branched configuration. Alternatively, if larger amounts of samples are needed, multiple amounts may be delivered to one well 36, as shown In FIG. 7B, without changing the settings on the pipettes. This, too, is accomplished by a structural channel 40 configuration. Many other configurations are possible.

It will be appreciated that the embodiments described hereinabove are described by way of example only and that numerous modifications thereto, all of which fall within the scope of the present invention, exist, For example, gels may be either vertical or horizontal. In addition, apertures may be on the side wall of the apparatus, rather than directly on the top cover. In one embodiment, the entire system is in a microscale range, in which case all the dimensions described hereinabove are reduced by a factor of 10–100.

It will be appreciated by persons skilled in the art that the present invention is not limited to what has been particularly shown and described hereinabove. Rather, the scope of the present invention is defined only by the claims that follow:

What is claimed is:

1. An apparatus for simultaneous loading of multiple samples for molecular separation, the apparatus comprising:
   a separation area having walls, wherein at least one of said walls comprises multiple apertures having loading sites;
   a gel located within said separation area; and
   a plurality of wells within said gel, wherein said apertures are connected to said plurality of wells by channels structurally configured to convey samples from said apertures to said wells,
   wherein said walls are pre-treated by water saturation.

2. An apparatus for simultaneous loading of multiple samples for molecular separation, the apparatus comprising:
   a separation area having walls, wherein at least one of said walls comprises multiple apertures having loading sites;
   a gel located within said separation area; and
   a plurality of wells within said gel,
   wherein said apertures are connected to said plurality of wells by channels structurally configured to convey samples from said apertures to said wells, wherein said apertures are structurally different from said wells, and
   wherein said structural difference includes a difference in shape.

3. An apparatus for simultaneous loading of multiple samples for molecular separation, the apparatus comprising:
   a separation area having walls, wherein at least one of said walls comprises multiple apertures having loading sites;
   a gel located within said separation area; and
   a plurality of wells within said gel,
   wherein said apertures are connected to said plurality of wells by channels structurally configured to convey samples from said apertures to said wells, wherein said apertures are structurally different from said wells, and wherein said structural difference includes a difference in alignment positions.

4. An apparatus for simultaneous loading of multiple samples for molecular separation, the apparatus comprising:
   a separation area having walls, wherein at least one of said walls comprises multiple apertures having loading sites;

a gel located within said separation area; and a plurality of wells within said gel, wherein said apertures are connected to said plurality of wells by channels structurally configured to convey samples from said apertures to said wells, wherein said channel configuration includes an incline.

5. An apparatus for simultaneous loading of multiple samples for molecular separation, the apparatus comprising:

a separation area having walls, wherein at least one of said walls comprises multiple apertures having loading sites;

a gel located within said separation area; and a plurality of wells within said gel, wherein said apertures are connected to said plurality of wells by channels structurally configured to convey samples from said apertures to said wells, wherein said channel configuration includes an irregular shape.

6. An apparatus for simultaneous loading of multiple samples for molecular separation, the apparatus comprising:

a separation area having walls, wherein at least one of said walls comprises multiple apertures having loading sites;

a gel located within said separation area; and a plurality of wells within said gel, wherein said apertures are connected to said plurality of wells by channels structurally configured to convey samples from said apertures to said wells, wherein said channel configuration includes a branched configuration.

7. An apparatus for electrophoresis separation, the apparatus comprising:

a substantially closed electrophoresis area;

an electrophoresis gel located within said electrophoresis area; and multiple rows of wells within said electrophoresis gel, wherein at least three rows of said multiple rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row.

8. An apparatus as in claim 7 further comprising at least one capture layer located within said electrophoresis gel.

9. An apparatus as in claim 8 wherein said at least one capture layer comprises part of a molecular recognition pair for separating said samples according to binding properties.

10. An apparatus as in claim 7 further comprising apertures having loading sites located above said wells.

11. An apparatus as in claim 10 wherein said loading sites are arranged in predetermined intervals.

12. An apparatus as in claim 11 wherein said predetermined intervals include 0.5–20 mm spacings.

13. An apparatus as in claim 11 wherein said predetermined intervals include 9 mm spacings.

14. An apparatus as in claim 11 wherein said predetermined intervals include 0.001 mm–1 mm spacings.

15. An apparatus as in claim 10 further comprising channels leading from said apertures to said wells.

16. A gel layer for molecular separation having a plurality of wells within said gel layer, wherein said wells are arranged in a plurality of spaced apart rows arranged in an alternating staggered format, wherein the wells of the odd rows are laterally offset by a predetermined distance in the same direction along the axes of said odd rows relative to the positions of the corresponding wells of the even rows along the axes of said even rows.

17. A gel layer as in claim 16 wherein said molecular separation includes electrophoresis separation by size.

18. A gel layer as in claim 16 wherein said molecular separation includes separation by binding.

19. A gel layer as in claim 16 wherein said molecular separation includes separation by size and by binding.

20. A gel layer as in claim 16 wherein said predetermined distance is in the range of 0.05–20 mm.

21. A gel layer as in claim 16 wherein said predetermined distance is 4.5 millimeters.

22. A device for delivering samples into wells for molecular separation, the device comprising:

a flat surface with a top side and a bottom side;

multiple loading sites located on said top side;

multiple apertures on said bottom side leading to said wells, wherein said apertures are arranged in a plurality of rows, at least three rows of said plurality of rows are arranged in an alternating staggered format such that at least the first aperture of the second row of said at least three rows is laterally offset in a first direction along the axis of said second row relative to the position of the first aperture of the first row of said at least three rows along the axis of said first row, and wherein at least the first aperture of at least the third row of said at least three rows is laterally offset in a second direction opposite said first direction along the axis of said at least third row relative to the position of said first aperture of said second row along the axis of said second row; and a channel through said flat surface connecting said loading sites to said apertures.

23. A device as in claim 22 wherein said molecular separation includes electrophoresis separation by size.

24. A device as in claim 22 wherein said molecular separation includes separation by binding.

25. A device as in claim 22 wherein said molecular separation includes separation by size and binding.

26. A device as in claim 22 wherein said loading sites are arranged in predetermined intervals.

27. A device as in claim 26 wherein said predetermined intervals include 0.5–20 mm spacings.

28. A device as in claim 26 wherein said predetermined intervals include 9 mm spacings.

29. A device as in claim 26 wherein said predetermined intervals include 0.001 mm–1 mm spacings.

30. A device as in claim 26 wherein said stagger format provides a running distance which is longer than the distance between two adjacent rows.

31. A device as in claim 26 wherein said channel includes an incline.

32. A device as in claim 26 wherein said channel includes an irregular shape.

33. A device as in claim 26 wherein said channel includes a branched configuration.

34. An apparatus for electrophoresis separation, the apparatus comprising:

a substantially closed electrophoresis area;

an electrophoresis gel with wells located within said electrophoresis area;

multiple rows of wells within said electrophoresis gel, wherein at least three rows of said multiple rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row; and at least one capture layer located within said gel.

35. An apparatus as in claim 34 wherein said at least one capture layer includes part of a molecular recognition pair for separating said samples according to binding properties.

36. An apparatus as in claim 34 further comprising apertures having loading sites located above said wells.

37. An apparatus as in claim 36 wherein said loading sites are arranged in predetermined intervals.

38. An apparatus as in claim 37 wherein said predetermined intervals include 0.5–20 mm spacings.

39. An apparatus as in claim 37 wherein said predetermined intervals include 9 mm spacings.

40. An apparatus as in claim 37 wherein said predetermined intervals include 0.001 mm–1 mm spacings.

41. An apparatus as in claim 36 further comprising channels leading from said apertures to said wells.

42. A system for conducting electrophoresis separation, the system comprising:

an electrical power source;

a substantially closed disposable cassette for conducting an electrophoresis separation therein and having conductive elements therein, said cassette comprising:

a body of gel for carrying therein said electrophoresis separation, a plurality of wells in said body of gel arranged in a plurality of rows, at least three rows of said plurality of rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row, and a plurality of apertures having loading sites leading to said plurality of wells; and a support for supporting said substantially closed cassette and for connecting said electrical power source to said conductive elements of said cassette.

43. A system according to claim 42 further comprising a light source, thereby enabling visualization of said electrophoresis separation while said cassette is in situ.

44. A system according to claim 43 wherein said light source is of variable wavelengths.

45. A system according to claim 44 wherein said light source is a UV light source, and said cassette comprises UV sensitive material capable of interacting with molecules undergoing electrophoresis separation and of emitting light.

46. A system according to claim 42 further comprising a calorimetric dye capable of interacting with molecules undergoing electrophoresis separation, thereby enabling to conduct said electrophoresis separation and to visualize it while said cassette is in situ.

47. A system according to claim 42 wherein said cassette is pre-treated by water saturation.

48. A system according to claim 42 further comprising camera means for documenting the results of said electrophoresis separation.

49. A system according to claim 42 wherein said support is configured to connect to one or more gels simultaneously.

50. A system according to claim 42 wherein said loading sites are spaced according to predetermined intervals for simultaneous loading of multiple samples.

51. A system according to claim 50 wherein said predetermined intervals include 9 mm spacings.

52. A system according to claim 42 further comprising at least one capture layer located within said gel.

53. A system according to claim 52 wherein said at least one capture layer includes part of a molecular recognition pair for separating said samples according to binding properties.

54. A method for simultaneous loading of multiple samples into an electrophoresis apparatus, the method comprising the steps of:

providing an electrophoresis apparatus having an area having at least a top wall defining said area and a gel within said area having multiple wells arranged in a plurality of rows, at least three rows of said plurality of rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row, wherein said top wall comprises apertures having loading sites and channels structurally configured to direct samples into said wells;

loading said samples into said loading sites with a standard multiple loading mechanism; and directing said samples, through said channels, from said loading sites to said wells.

55. A method as in claim 54 wherein said standard multiple loading mechanism includes a microtiter multi-pipette.

56. A method as in claim 55 wherein said microtiter multi-pipette includes a 96-well microtiter format.

57. A method for molecular separation, the method comprising the steps of:

providing an apparatus having a separation area having at least a top wall defining a separation chamber and a gel within said chamber having multiple wells arranged in a plurality of rows, at least three rows of said plurality of rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row, wherein said top wall comprises apertures having loading sites and channels structurally configured to direct samples into said wells;

loading said samples into said loading sites with a standard multiple loading mechanism;

directing said samples from said loading sites to said wells;

providing an electrical current through said separation area so as to allow for separation of said samples; and separating said samples according to predefined properties.

58. A method as in claim 57 wherein said predefined properties include size.

59. A method as in claim 57 wherein said predefined properties include binding properties.

60. A method as in claim 57 wherein said predefined properties include size and binding properties.

61. A method as in claim 57 wherein said standard multiple loading mechanism includes a microtiter multi-pipette.

62. A method as in claim 61 wherein said microtiter multi-pipette includes a 96-well microtiter format.

63. A gel layer for molecular separation having a plurality of wells within said gel layer, said wells are arranged in a plurality of rows, at least three rows of said plurality of rows are arranged in an alternating staggered format such that at least the first well of the second row of said at least three rows is laterally offset in a first direction along the axis of said second row relative to the position of the first well of the first row of said at least three rows along the axis of said first row, and wherein at least the first well of at least the third row of said at least three rows is laterally offset in a second direction opposite said first direction along the axis of said at least third row relative to the position of said first well of said second row along the axis of said second row.

* * * * *

UNITED STATES PATENT AND TRADEMARK OFFICE
CERTIFICATE OF CORRECTION

PATENT NO.     : 6,562,213 B1
DATED          : May 13, 2003
INVENTOR(S)    : Shmuel Cabilly et al.

It is certified that error appears in the above-identified patent and that said Letters Patent is hereby corrected as shown below:

<u>Column 10,</u>
Lines 21 and 38, please replace "surface" with -- wall --
Line 38, please replace "a channel" with -- channels --

Signed and Sealed this

Ninth Day of March, 2004

JON W. DUDAS
*Acting Director of the United States Patent and Trademark Office*